(12) United States Patent
Kandimalla et al.

(10) Patent No.: US 8,153,605 B2
(45) Date of Patent: Apr. 10, 2012

(54) MODULATION OF TOLL-LIKE RECEPTOR 3 EXPRESSION BY ANTISENSE OLIGONUCLEOTIDES

(75) Inventors: Ekambar Kandimalla, Southboro, MA (US); Mallikarjuna Putta, Burlington, MA (US); Lakshmi Bhagat, Framingham, MA (US); Daqing Wang, Bedford, MA (US); Dong Yu, Westboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 175 days.

(21) Appl. No.: 12/534,911

(22) Filed: Aug. 4, 2009

(65) Prior Publication Data

US 2010/0041735 A1 Feb. 18, 2010

Related U.S. Application Data

(60) Provisional application No. 61/086,026, filed on Aug. 4, 2008.

(51) Int. Cl.
*C12N 15/11* (2006.01)
*C12Q 1/68* (2006.01)
*C07H 21/04* (2006.01)

(52) U.S. Cl. ....... 514/44 A; 435/6.1; 536/23.1; 536/24.5
(58) Field of Classification Search .................. None
See application file for complete search history.

(56) References Cited

U.S. PATENT DOCUMENTS

| | | | |
|---|---|---|---|
| 2004/0132079 A1 | 7/2004 | Gupta et al. | |
| 2005/0214823 A1* | 9/2005 | Blume et al. ................ | 435/6 |
| 2008/0124365 A1* | 5/2008 | Kim .......................... | 424/278.1 |
| 2008/0161256 A1 | 7/2008 | Morrisey et al. | |

OTHER PUBLICATIONS

Akira, S. (2003) J. Biol. Chem. 278:38105.
Akira, S. et al. (2001) Nature Immunol. 2:675-680.
Alexopoulou, L. (2001) Nature 413:732-738.
Applequist, et al. (2002) Int. Immunol. 14:pp. 1065-1074.
Barrat and Coffman (2008) Immunol. Rev. 223:271-283.
Bock LC et al., Nature, 355:564-6, 1992.
Caricilli et al. (2008) J. Endocrinology 199:399.
Chen, Y., et al., Gene Ther. 8: 1024-1032 (2001).
Cook, D.N. et al. (2004) Nature Immunol. 5:975-979.
Diebold (2008) Adv. Drug Deliv. Rev. 60:813-823.
Diebold, S.S. et al. (2004) Science 303:1529-1531.
Duffy, K et al. (2007) Cell Immunol. 248:103-114.
Gao et al. (2008) Semin. Immunopathol. 30:29-40.
Geller at al. (2008) Curr. Drug Dev. Tech. 5:29-38.
Gursel, I., et al. J. Immunol., 171: 1393-1400 (2003).
Hemmi H et al. (2002) Nat Immunol 3:196-200.
Hornung, V. et al., (2002) J. Immunol. 168:4531-4537.
Huang et al. (2005) Cancer Res. 65:5009-5014.
Huang et al. (2005) Invest. Opthal. Vis. Sci. 46:4209-4216.
Iyer et al. (1995) Tetrahedron Asymmetry 6:1051-1054.
Jurk M et al., (2002) Nat Immunol 3:499.
Krieg, A. M. (2002) Annu. Rev. Immunol. 20:709.
Lee et al. (2008) Semin. Immunopathol. 30:3-9.
Lee J et al. (2003) Proc. Natl. Acad. Sci. USA 100:6646-6651.
Lenert, P. et al. (2003) DNA Cell Biol. 22(10):621-631.
Liew, F. et al. (2005) Nature 5:446-458.
Medzhitov, R. (2001) Nature Rev. Immunol. 1: 135-145.
Padmanabhan, K et al., J Biol Chem., 268(24):17651-4, 1993.
Papadimitraki et al. (2007) J. Autoimmun. 29: 310-318.
Patole, P. et al. (2005) J. Am. Soc. Nephrol. 16:3273-3280.
Rock, et al. (1998) Proc. Natl. Acad. Sci. 95: 588-593.
Robert et al. (2008) Semin. Immunopathol. 30:41-51.
Shirota, H., et al., J. Immunol., 173: 5002-5007 (2004).
Stunz, L.L., Eur. J. Immunol. (2002) 32: 1212-1222.
Sun et al. (2007) Inflam. Allergy Drug Targets 6:223-235.
Tang et al. (1993) Nucleic Acids Res. 20:2729-2735.
Tobias & Curtiss (2008) Semin. Immunopathol. 30:23-27.
Trinchieri and Sher (2007) Nat. Rev. Immunol. 7:179-190.
Tse and Homer (2008) Semin. Immunopathol. 30:53-62.
Vijay-Kumar et al. (2008) Semin. Immunopathol. 30:11-21.

\* cited by examiner

*Primary Examiner* — Doug Schultz
(74) *Attorney, Agent, or Firm* — McDonnell Boehnen Hulbert & Berghoff LLP

(57) ABSTRACT

Antisense oligonucleotide compounds, compositions and methods are provided for down regulating the expression of TLR3. The compositions comprise antisense oligonucleotides targeted to nucleic acids encoding TLR3. The compositions may also comprise antisense oligonucleotides targeted to nucleic acids encoding TLR3 in combination with other therapeutic and/or prophylactic compounds and/or compositions. Methods of using these compounds and compositions for down-regulating TLR3 expression and for prevention or treatment of diseases wherein modulation of TLR3 expression would be beneficial are provided.

30 Claims, 4 Drawing Sheets

Linear Synthesis

NF-κB activation expressed as fold control (Mean+/-SD) in human TLR3-HEK293XL cells

| Treatment SEQ ID NO. | | Antisense alone | Antisense + PolyI.PolyC (TLR3 agonist) (25 µg/ml) |
|---|---|---|---|
| PBS | | 1.00+/- 0.82 | 19.29+/-1.18 |
| 11 | 1 µg/ml | 1.75+/- 0.47 | 8.46+/-0.18 |
| 11 | 10 µg/ml | 1.04+/- 0.53 | 1.88+/-0.29 |
| 63 | 1 µg/ml | 0.67+/- 0.94 | 5.88+/-0.29 |
| 63 | 10 µg/ml | 1.79+/- 0.77 | 1.25+/-0.24 |
| 88 | 1 µg/ml | 1.13+/- 0.77 | 12.92+/-0.35 |
| 88 | 10 µg/ml | 0.50+/- 0.82 | 5.50+/-0.12 |
| 144 | 1 µg/ml | 1.83+/-1.06 | 13.46+/-1.06 |
| 144 | 10 µg/ml | 0.79+/-0.77 | 4.96+/-0.41 |

Figure 2

| SEQ ID NO. | IL-12 production (pg/ml) | % Inhibition of TLR3 agonist activity |
|---|---|---|
| Naïve sera | 1,830 | |
| 162 alone | 1,631 | |
| 163 alone | 1,631 | |
| 164 alone | 979 | |
| 165 alone | 979 | |
| TLR3 agonist alone (poyI.polyC) | 22,059 | |
| 162 + TLR3 agonist | 8,509 | 61.4 |
| 163 + TLR3 agonist | 20,169 | 8.6 |
| 164 + TLR3 agonist | 4,734 | 78.5 |
| 165 + TLR3 agonist | 18,047 | 18.2 |

Figure 3

Figure 4
SEQ ID NO: 162

```
   1    CACTTTCGAG AGTGCCGTCT ATTTGCCACA CACTTCCCTG ATGAAATGTC TGGATTTGGA
  61    CTAAAGAAAA AAGGAAAGGC TAGCAGTCAT CCAACAGAAT CATGAGACAG ACTTTGCCTT
 121    GTATCTACTT TTGGGGGGGC CTTTTGCCCT TTGGGATGCT GTGTGCATCC TCCACCACCA
 181    AGTGCACTGT TAGCCATGAA GTTGCTGACT GCAGCCACCT GAAGTTGACT CAGGTACCCG
 241    ATGATCTACC CACAAACATA ACAGTGTTGA ACCTTACCCA TAATCAACTC AGAAGATTAC
 301    CAGCCGCCAA CTTCACAAGG TATAGCCAGC TAACTAGCTT GGATGTAGGA TTTAACACCA
 361    TCTCAAAACT GGAGCCAGAA TTGTGCCAGA AACTTCCCAT GTTAAAAGTT TTGAACCTCC
 421    AGCACAATGA GCTATCTCAA CTTTCTGATA AAACCTTTGC CTTCTGCACG AATTTGACTG
 481    AACTCCATCT CATGTCCAAC TCAATCCAGA AAATTAAAAA TAATCCCTTT GTCAAGCAGA
 541    AGAATTTAAT CACATTAGAT CTGTCTCATA ATGGCTTGTC ATCTACAAAA TTAGGAACTC
 601    AGGTTCAGCT GGAAAATCTC AAGAGCTTC TATTATCAAA CAATAAAATT CAAGCGCTAA
 661    AAAGTGAAGA ACTGGATATC TTTGCCAATT CATCTTTAAA AAAATTAGAG TTGTCATCGA
 721    ATCAAATTAA AGAGTTTTCT CCAGGGTGTT TTCACGCAAT GGAAGATTA TTTGGCCTCT
 781    TTCTGAACAA TGTCCAGCTG GGTCCCAGCC TTACAGAGAA GCTATGTTTG GAATTAGCAA
 841    ACACAAGCAT TCGGAATCTG TCTCTGAGTA ACAGCCAGCT GTCCACCACC AGCAATACAA
 901    CTTTCTTGGG ACTAAAGTGG ACAAATCTCA CTATGCTCGA TCTTTCCTAC AACAACTTAA
 961    ATGTGGTTGG TAACGATTCC TTTGCTTGGC TTCCACAACT AGAATATTTC TTCCTAGAGT
1021    ATAATAATAT ACAGCATTTG TTTTCTCACT CTTTGCACGG GCTTTTCAAT GTGAGGTACC
1081    TGAATTTGAA ACGGTCTTTT ACTAAACAAA GTATTTCCCT TGCCTCACTC CCCAAGATTG
1141    ATGATTTTTC TTTTCAGTGG CTAAAATGTT TGGAGCACCT TAACATGGAA GATAATGATA
1201    TTCCAGGCAT AAAAAGCAAT ATGTTCACAG GATTGATAAA CCTGAAATAC TTAAGTCTAT
1261    CCAACTCCTT TACAAGTTTG CGAACTTTGA CAAATGAAAC ATTTGTATCA CTTGCTCATT
1321    CTCCCTTACA CATACTCAAC CTAACCAAGA ATAAAATCTC AAAAATAGAG AGTGATGCTT
1381    TCTCTTGGTT GGGCCACCTA GAAGTACTTG ACCTGGGCCT TAATGAAATT GGGCAAGAAC
1441    TCACAGGCCA GGAATGGAGA GGTCTAGAAA ATATTTTCGA AATCTATCTT TCCTACAACA
1501    AGTACCTGCA GCTGACTAGG AACTCCTTTG CCTTGGTCCC AAGCCTTCAA CGACTGATGC
1561    TCCGAAGGGT GGCCCTTAAA AATGTGGATA GCTCTCCTTC ACCATTCCAG CCTCTTCGTA
1621    ACTTGACCAT TCTGGATCTA AGCAACAACA ACATAGCCAA CATAAATGAT GACATGTTGG
1681    AGGGTCTTGA GAAACTAGAA ATTCTCGATT GCAGCATAA CAACTTAGCA CGGCTCTGGA
1741    AACACGCAAA CCCTGGTGGT CCCATTTATT TCCTAAAGGG TCTGTCTCAC CTCCACATCC
1801    TTAACTTGGA GTCCAACGGC TTTGACGAGA TCCCAGTTGA GGTCTTCAAG GATTTATTTG
1861    AACTAAAGAT CATCGATTTA GGATTGAATA ATTTAAACAC ACTTCCAGCA TCTGTCTTTA
1921    ATAATCAGGT GTCTCTAAAG TCATTGAACC TTCAGAAGAA TCTCATAACA TCCGTTGAGA
1981    AGAAGGTTTT CGGGCCAGCT TCAGGAACC TGACTGAGTT AGATATGCGC TTAATCCCT
2041    TTGATTGCAC GTGTGAAAGT ATTGCCTGGT TTGTTAATTG GATTAACGAG ACCCATACCA
2101    ACATCCCTGA GCTGTCAAGC CACTACCTTT GCAACACTCC ACCTCACTAT CATGGGTTCC
2161    CAGTGAGACT TTTTGATACA TCATCTTGCA AAGACAGTGC CCCCTTTGAA CTCTTTTTCA
2221    TGATCAATAC CAGTATCCTG TTGATTTTTA TCTTTATTGT ACTTCTCATC CACTTTGAGG
2281    GCTGGAGGAT ATCTTTTTAT TGGAATGTTT CAGTACATCG AGTTCTTGGT TTCAAAGAAA
2341    TAGACAGACA GACAGAACAG TTTGAATATG CAGCATATAT AATTCATGCC TATAAAGATA
2401    AGGATTGGGT CTGGGAACAT TTCTCTTCAA TGGAAAAGGA AGACCAATCT CTCAAATTTT
2461    GTCTGGAAGA AAGGGACTTT GAGGCGGGTG TTTTTGAACT AGAAGCAATT GTTAACAGCA
2521    TCAAAAGAAG CAGAAAAATT ATTTTTGTTA TAACACACCA TCTATTAAAA GACCCATTAT
2581    GCAAAAGATT CAAGGTACAT CATGCAGTTC AACAAGCTAT TGAACAAAAT CTGGATTCCA
2641    TTATATTGGT TTTCCTTGAG GAGATTCCAG ATTATAAACT GAACCATGCA CTCTGTTTGC
2701    GAAGAGGAAT GTTTAAATCT CACTGCATCT TGAACTGGCC AGTTCAGAAA GAACGGATAG
2761    GTGCCTTTCG TCATAAATTG CAAGTAGCAC TTGGATCCAA AAACTCTGTA CATTAAATTT
2821    ATTTAAATAT TCAATTAGCA AAGGAGAAAC TTTCTCAATT TAAAAAGTTC TATGGCAAAT
2881    TTAAGTTTTC CATAAAGGTG TTATAATTTG TTTATTCATA TTTGTAAATG ATTATATTCT
2941    ATCACAATTA CATCTCTTCT AGGAAAATGT GTCTCCTTAT TCAGGCCTA TTTTTGACAA
3001    TTGACTTAAT TTTACCCAAA ATAAAACATA TAAGCACGTA AAAAAAAAAA AAAAAA
```

MODULATION OF TOLL-LIKE RECEPTOR 3 EXPRESSION BY ANTISENSE OLIGONUCLEOTIDES

RELATED APPLICATIONS

This application claims the benefit of prior U.S. Provisional Patent Application Ser. No. 61/086,026, filed on Aug. 4, 2008, the contents of which are incorporated by reference in its entirety.

BACKGROUND OF THE INVENTION

1. Field of the Invention

The present invention relates to Toll-Like Receptor 3 (TLR3). In particular, the invention relates to antisense oligonucleotides that specifically hybridize with nucleic acids encoding TLR3, thus modulating TLR3 expression and activity, and their use in treating or preventing diseases associated with TLR3 or wherein modulation of TLR3 expression would be beneficial.

2. Summary of the Related Art

Toll-like receptors (TLRs) are present on many cells of the immune system and have been shown to be involved in the innate immune response (Hornung, V. et al., (2002) J. Immunol. 168:4531-4537). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1: 135-145). In vertebrates, this family consists of at least 11 proteins called TLR1 to TLR11, which are known to recognize pathogen associated molecular patterns (PAMP) from bacteria, fungi, parasites and viruses and induce an immune response mediated by a number of transcription factors.

Some TLRs are located on the cell surface to detect and initiate a response to extracellular pathogens and other TLRs are located inside the cell to detect and initiate a response to intracellular pathogens. Table 1 provides a representation of TLRs, the known agonists therefore and the cell types known to contain the TLR (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413:732-738).

TABLE 1

| TLR Molecule | Agonist | Cell Types Containing Receptor |
|---|---|---|
| Cell Surface TLRs: | | |
| TLR2 | bacterial lipopeptides | Monocytes/macrophages Myeloid dendritic cells Mast cells |
| TLR4 | gram negative bacteria | Monocytes/macrophages Myeloid dendritic cells Mast cells Intestinal epithelium |
| TLR5 | motile bacteria | Monocyte/macrophages Dendritic cells Intestinal epithelium |
| TLR6 | gram positive bacteria | Monocytes/macrophages Mast cells B lymphocytes |
| Endosomal TLRs: | | |
| TLR3 | double stranded RNA viruses | Dendritic cells B lymphocytes |
| TLR7 | single stranded RNA viruses; RNA-immunoglobulin complexes | Monocytes/macrophages Plasmacytoid dendritic cells B lymphocytes |
| TLR8 | single stranded RNA viruses; RNA-immunoglobulin complexes | Monocytes/macrophages Dendritic cells Mast cells |
| TLR9 | DNA containing unmethylated "CpG" motifs; DNA-immunoglobulin complexes | Monocytes/macrophages Plasmacytoid dendritic cells B lymphocytes |

The signal transduction pathway mediated by the interaction between a ligand and a TLR is shared among most members of the TLR family and involves a toll/IL-1 receptor (TIR domain), the myeloid differentiation marker 88 (MyD88), IL-1R-associated kinase (IRAK), interferon regulating factor (IRF), TNF-receptor-associated factor (TRAF), TGFβ-activated kinase1, IκB kinases, IκB, and NF-κB (see for example: Akira, S. (2003) J. Biol. Chem. 278:38105 and Geller at al. (2008) Curr. Drug Dev. Tech. 5:29-38). More specifically, for TLRs 1, 2, 4, 5, 6, 7, 8, 9 and 11, this signaling cascade begins with a PAMP ligand interacting with and activating the membrane-bound TLR, which exists as a homo-dimer in the endosomal membrane or the cell surface. Following activation, the receptor undergoes a conformational change to allow recruitment of the TIR domain containing protein MyD88, which is an adapter protein that is common to all TLR signaling pathways except TLR3. MyD88 recruits IRAK4, which phosphorylates and activates IRAK1. The activated IRAK1 binds with TRAF6, which catalyzes the addition of polyubiquitin onto TRAF6. The addition of ubiquitin activates the TAK/TAB complex, which in turn phosphorylates IRFs, resulting in NF-kB release and transport to the nucleus. NF-kB in the nucleus induces the expression of proinflammatory genes (see for example, Trinchieri and Sher (2007) Nat. Rev. Immunol. 7:179-190).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs. TLR3 is known to localize in endosomes inside the cell and recognizes nucleic acids (DNA and RNA) and small molecules such as nucleosides and nucleic acid metabolites. TLR3 has been shown to recognize and respond to double stranded RNA viruses (Diebold, S. S., et al., (2004) Science 303:1529-1531). In addition to naturally existing ligands for TLR3, certain synthetic oligonucleotide analogs have been shown to activate TLR3. For example, poly(I:C), a double stranded RNA, has been shown to activate TLR3, resulting in a concomitant induction of interferon (Alexopoulou, L. (2001) Nature 413:732-738).

As a result of their involvement in regulating an inflammatory response, TLRs have been shown to play a role in the pathogenesis of many diseases, including autoimmunity, infectious disease and inflammation (Papadimitraki et al. (2007) J. Autoimmun. 29: 310-318; Sun et al. (2007) Inflam. Allergy Drug Targets 6:223-235; Diebold (2008) Adv. Drug Deliv. Rev. 60:813-823; Cook, D. N. et al. (2004) Nature Immunol. 5:975-979; Tse and Horner (2008) Semin. Immunopathol. 30:53-62; Tobias & Curtiss (2008) Semin. Immunopathol. 30:23-27; Ropert et al. (2008) Semin. Immunopathol. 30:41-51; Lee et al. (2008) Semin. Immunopathol. 30:3-9; Gao et al. (2008) Semin. Immunopathol. 30:29-40; Vijay-Kumar et al. (2008) Semin. Immunopathol. 30:11-21). While activation of TLRs is involved in mounting an immune response, an uncontrolled or undesired stimulation of the immune system through TLRs may exacerbate certain diseases in immune compromised subjects or may cause unwanted immune stimulation. Thus, down-regulating TLR expression and/or activity may provide a useful means for disease intervention.

To date, investigative strategies aimed selectively at inhibiting TLR activity have involved small molecules (WO/2005/007672), antibodies (see for example: Duffy, K. et al. (2007) Cell Immunol. 248:103-114), catalytic RNAi technologies (e.g. small inhibitory RNAs), certain antisense molecules (Caricilli et al. (2008) J. Endocrinology 199:399), and competitive inhibition with modified or methylated oligonucleotides (see for example: Kandimalla et al. US2008/0089883; Barrat and Coffman (2008) Immunol. Rev. 223:271-283). For example, chloroquine and hydroxylchloroquine have been shown to block endosomal-TLR signaling by down-regulating the maturation of endosomes (Krieg, A. M. (2002) Annu. Rev. Immunol. 20:709). Also, Huang et al. have shown the use of TLR4 siRNA to reverse the tumor-mediated suppression of T cell proliferation and natural killer cell activity (Huang et al. (2005) Cancer Res. 65:5009-5014), and the use of TLR9 siRNA to prevent bacterial-induced inflammation of the eye (Huang et al. (2005) Invest. Opthal. Vis. Sci. 46:4209-4216).

Additionally, several groups have used synthetic oligodeoxynucleotides having two triplet sequences, a proximal "CCT" triplet and a distal "GGG" triplet, a poly "G" (e.g. "GGGG" or "GGG") or "GC" sequences that interact with certain intracellular proteins, resulting in the inhibition of TLR signaling and the concomitant production and release of pro-inflammatory cytokines (see for example: Lenert, P. et al. (2003) DNA Cell Biol. 22(10):621-631; Patole, P. et al. (2005) J. Am. Soc. Nephrol. 16:3273-3280; Gursel, I., et al. (J. Immunol., 171: 1393-1400 (2003), Shirota, H., et al., J. Immunol., 173: 5002-5007 (2004), Chen, Y., et al., Gene Ther. 8: 1024-1032 (2001); Stunz, L. L., Eur. J. Immunol. (2000) 32: 1212-1222; Kandimalla et al. WO2007/7047396). However, oligonucleotides containing guanosine strings have been shown to form tetraplex structures, act as aptamers and inhibit thrombin activity (Bock L C et al., Nature, 355:564-6, 1992; Padmanabhan, K et al., J Biol Chem., 268(24):17651-4, 1993). Thus, the utility of these inhibitory oligodeoxynucleotide molecules may not be achievable in patients.

A potential approach to "knock down" expression of TLRs is antisense technology. The history of antisense technology has revealed that while discovery of antisense oligonucleotides that inhibit gene expression is relatively straight forward, the optimization of antisense oligonucleotides that have true potential as clinical candidates is not. Accordingly, if an antisense approach to down-regulating TLR3 is to be successful, there is a need for optimized antisense oligonucleotides that most efficiently achieve this result. Such optimized antisense oligonucleotides could be used alone, or in conjunction with the antagonists of Kandimalla et al., or other therapeutic approaches.

BRIEF SUMMARY OF THE INVENTION

The present invention is directed to optimized synthetic antisense oligonucleotides that are targeted to a nucleic acid encoding TLR3 and that efficiently inhibit the expression of TLR3 through inhibition of mRNA translation and/or through an RNase H mediated mechanism.

In a first aspect, optimized antisense oligonucleotides according to the invention include those having SEQ ID NOs: 11, 12, 18, 26, 47, 63, 78, 88, 92, 110, 114 or 144.

In a second aspect, the invention provides a composition comprising at least one optimized antisense oligonucleotide according to the invention and a physiologically acceptable carrier, diluent or excipient.

In a third aspect, the invention provides a method of inhibiting TLR3 expression. In this method, an oligonucleotide or multiple oligonucleotides of the invention are specifically contacted or hybridized with TLR3 mRNA either in vitro or in a cell.

In a fourth aspect, the invention provides methods for inhibiting the expression of TLR3 in a mammal, particularly a human, such methods comprising administering to the mammal a compound or composition according to the invention.

In a fifth aspect, the invention provides a method for inhibiting a TLR3-mediated immune response in a mammal, the method comprising administering to the mammal a TLR3 antisense oligonucleotide according to the invention in a pharmaceutically effective amount.

In a sixth aspect, the invention provides a method for therapeutically treating a mammal having a disease mediated by TLR3, such method comprising administering to the mammal, particularly a human, a TLR3 antisense oligonucleotide of the invention, or a composition thereof, in a pharmaceutically effective amount.

In a seventh aspect, the invention provides methods for preventing a disease or disorder in a mammal, particularly a human, at risk of contracting or developing a disease or disorder mediated by TLR3. The method according to this aspect of the invention comprises administering to the mammal an antisense oligonucleotide according to the invention, or a composition thereof, in a prophylactically effective amount.

In an eighth aspect, the invention provides methods for down-regulating TLR3 expression and thus preventing the "off-target" activity of double-stranded or partially double stranded RNA molecules (hereinafter, collectively, "dsRNA"), or other compounds or drugs that have a side effect of activating TLR3. For example, the TLR3 antisense oligonucleotide according to the invention can be administered in combination with one or dsRNA-containing compounds, which are not directed to the same target as the antisense molecule of the invention, and which comprise an immunostimulatory motif that would activate a TLR3-mediated immune response but for the presence of the TLR3 antisense oligonucleotide according to the invention.

In a ninth aspect, the invention provides a method for inhibiting TLR3 expression and activity in a mammal, comprising administering to the mammal an antisense oligonucleotide complementary to TLR3 mRNA and an antagonist of TLR3 protein, a kinase inhibitor or an inhibitor of STAT (signal transduction and transcription) protein.

The subject oligonucleotides and methods of the invention are also useful for examining the function of the TLR3 gene in a cell or in a control mammal or in a mammal afflicted with a disease associated with TLR3 or immune stimulation through TLR3. The cell or mammal is administered the oligonucleotide, and the expression of TLR3 mRNA or protein is examined.

BRIEF DESCRIPTION OF THE DRAWINGS

FIG. 2 is a graphical representation of the activity of exemplar human TLR3 antisense oligonucleotides according to the invention in HEK293XL cells expressing human TLR3. The data demonstrate the ability of exemplar oligonucleotides according to the invention to inhibit TLR3 expression and activation in HEK293 cells that were cultured and treated according to Example 2.

FIG. 3 is a graphical representation of the activity of exemplar TLR3 antisense oligonucleotides according to the invention to inhibit TLR3-induced IL-12 following in vivo administration according to example 3. The data demonstrate that administration of an exemplar TLR3 antisense oligonucleotide according to the invention can cause down-regulation of TLR3 expression in vivo and prevent the induction of IL-12 by a TLR3 agonist. More generally, the data demonstrate the ability of a TLR3 antisense oligonucleotide according to the invention to inhibit the induction of pro-inflammatory cytokines by a TLR3 agonist.

FIG. 4 shows the nucleotide sequence of human TLR3 mRNA [SEQ. ID. NO.: 162] (Genbank Accession No. NM 003265).

DETAILED DESCRIPTION OF THE PREFERRED EMBODIMENTS

Figure 1:
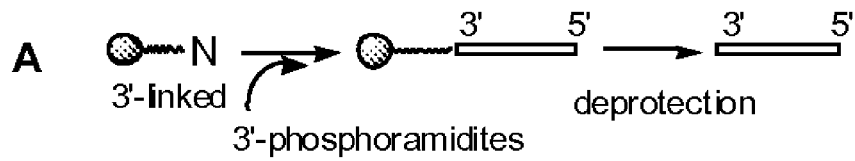
FIG. 1 is a synthetic scheme for the linear synthesis of antisense oligonucleotides of the invention. DMTr=4,4'-dimethoxytrityl; CE=cyanoethyl.
Figure 1:
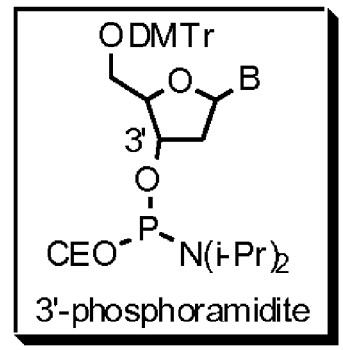
Figure 1:
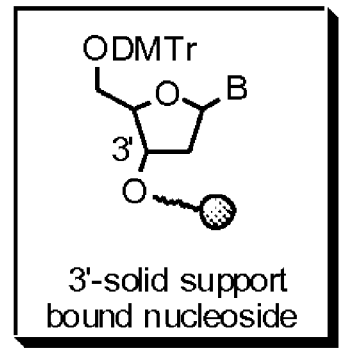

The invention relates to optimized TLR3 antisense oligonucleotides, compositions comprising such oligonucleotides and methods of their use for inhibiting or suppressing a TLR9-mediated immune response. The antisense oligonucleotides according to the invention are stable, specific and do not activate an innate immune response, thereby overcoming the problems of certain previously attempted approaches. Pharmaceutical and other compositions comprising the compounds according to the invention are also provided. Further provided are methods of down-regulating the expression of TLR3 in cells or tissues comprising contacting said cells or tissues with one or more of the antisense compounds or compositions of the invention alone or in combination with other prophylactic or therapeutic compositions.

Specifically, the invention provides antisense oligonucleotides designed to be complementary to a genomic region or an RNA molecule transcribed therefrom. These TLR3 antisense oligonucleotides have unique sequences that target specific, particularly available mRNA sequences, resulting in maximally effective inhibition or suppression of TLR3-mediated signaling in response to endogenous and/or exogenous TLR3 ligands or TLR3 agonists.

The TLR3 antisense oligonucleotides according to the invention inhibit immune responses induced by natural or artificial TLR3 agonists in various cell types and in various in vitro and in vivo experimental models. As such, the antisense compositions according to the invention are useful as tools to study the immune system, as well as to compare the immune systems of various animal species, such as humans and mice.

Further provided are methods of treating an animal, particularly a human, having, suspected of having, or being prone to develop a disease or condition associated with TLR3 activation by administering a therapeutically or prophylactically effective amount of one or more of the antisense compounds or compositions of the invention. These can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, malaria, and bacteria, parasitic, and viral infections in adult and pediatric human and veterinary applications. In addition, TLR3 antisense oligonucleotides of the invention are useful in the prevention and/or treatment of various diseases, either alone, in combination with or co-administered with other drugs or prophylactic or therapeutic compositions, for example, DNA vaccines, antigens, antibodies, and allergens; and in combination with chemotherapeutic agents (both traditional chemotherapy and modern targeted therapies) and/or TLR3 antagonists for prevention and treatment of diseases. TLR3 antisense oligonucleotides of the invention are useful in combination with compounds or drugs that have unwanted TLR3-mediated immune stimulatory properties.

The patents and publications cited herein reflect the level of knowledge in the art and are hereby incorporated by reference in their entirety. Any conflict between the teachings of these patents and publications and this specification shall be resolved in favor of the latter.

The foregoing and other objects of the present invention, the various features thereof, as well as the invention itself may be more fully understood from the following description, when read together with the accompanying drawings in which:

The term "2'-O-substituted" means substitution of the 2' position of the pentose moiety with an —O— lower alkyl group containing 1-6 saturated or unsaturated carbon atoms (for example, but not limited to, 2'-O-methyl), or with an —O-aryl or allyl group having 2-6 carbon atoms, wherein such alkyl, aryl or allyl group may be unsubstituted or may be substituted, (for example, with 2'-O-ethoxy-methyl, halo, hydroxy, trifluoromethyl, cyano, nitro, acyl, acyloxy, alkoxy, carboxyl, carbalkoxyl, or amino groups); or with a hydroxy, an amino or a halo group, but not with a 2'-H group. In some embodiments of the invention the oligonucleotides of the invention include four or five ribonucleotides 2'-O-alkylated at their 5' terminus (i.e., 5' 2-O-alkylated ribonucleotides), and/or four or five ribonucleotides 2'-O-alkylated at their 3' terminus (i.e., 3' 2-O-alkylated ribonucleotides). In exemplar embodiments, the nucleotides of the synthetic oligonucleotides are linked by at least one phosphorothioate internucleotide linkage. The phosphorothioate linkages may be mixed Rp and Sp enantiomers, or they may be stereoregular or substantially stereoregular in either Rp or Sp form (see Iyer et al. (1995) Tetrahedron Asymmetry 6:1051-1054).

The term "3'", when used directionally, generally refers to a region or position in a polynucleotide or oligonucleotide 3' (toward the 3' end of the nucleotide) from another region or position in the same polynucleotide or oligonucleotide.

The term "5'", when used directionally, generally refers to a region or position in a polynucleotide or oligonucleotide 5' (toward the 5' end of the nucleotide) from another region or position in the same polynucleotide or oligonucleotide.

The term "about" generally means that the exact number is not critical. Thus, oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "antagonist" generally refers to a substance that attenuates the effects of an agonist.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (Nexavar®), Sutent®, dasatinib, Dasatinib™, Zactima™, Tykerb™ and STI571.

The term "airway inflammation" generally includes, without limitation, inflammation in the respiratory tract caused by allergens, including asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule.

The term "allergy" generally includes, without limitation, food allergies, respiratory allergies and skin allergies.

The term "antigen" generally refers to a substance that is recognized and selectively bound by an antibody or by a T cell antigen receptor. Antigens may include but are not limited to peptides, proteins, nucleosides, nucleotides and combinations thereof. Antigens may be natural or synthetic and generally induce an immune response that is specific for that antigen.

The term "autoimmune disorder" generally refers to disorders in which "self" antigen undergo attack by the immune system. Such term includes, without limitation, lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis autoimmune asthma, septic shock and psoriasis.

The term "cancer" generally refers to, without limitation, any malignant growth or tumor caused by abnormal or uncontrolled cell proliferation and/or division. Cancers may occur in humans and/or mammals and may arise in any and all tissues. Treating a patient having cancer may include administration of a compound, pharmaceutical formulation or vaccine according to the invention such that the abnormal or uncontrolled cell proliferation and/or division, or metastasis is affected.

The term "carrier" generally encompasses any excipient, diluent, filler, salt, buffer, stabilizer, solubilizer, oil, lipid, lipid containing vesicle, microspheres, liposomal encapsulation, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, for example, *Remington's Pharmaceutical Sciences*, 18th Edition, ed. A. Gennaro, Mack Publishing Co., Easton, Pa., 1990.

The term "co-administration" or "co-administered" generally refers to the administration of at least two different substances sufficiently close in time to modulate an immune response. Co-administration refers to simultaneous administration, as well as temporally spaced order of up to several days apart, of at least two different substances in any order, either in a single dose or separate doses.

The term "in combination with" generally means administering a compound according to the invention and another agent useful for treating the disease or condition that does not abolish TLR3 antisense activity of the compound in the course of treating a patient. Such administration may be done in any order, including simultaneous administration, as well as temporally spaced order from a few seconds up to several days apart. Such combination treatment may also include more than a single administration of the compound according to the invention and/or independently the other agent. The administration of the compound according to the invention and the other agent may be by the same or different routes.

The term "individual" or "subject" or "vertebrate" generally refers to a mammal, such as a human.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "mammal" is expressly intended to include warm blooded, vertebrate animals, including, without limitation, humans, non-human primates, rats, mice, cats, dogs, horses, cattle, cows, pigs, sheep and rabbits.

The term "nucleoside" generally refers to compounds consisting of a sugar, usually ribose or deoxyribose, and a purine or pyrimidine base.

The term "nucleotide" generally refers to a nucleoside comprising a phosphorous-containing group attached to the sugar.

The term "modified nucleoside" generally is a nucleoside that includes a modified heterocyclic base, a modified sugar moiety, or any combination thereof. In some embodiments, the modified nucleoside is a non-natural pyrimidine or purine nucleoside, as herein described. For purposes of the invention, a modified nucleoside, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil and a sugar is considered to be non-natural if it is not β-ribo-furanoside or 2'-deoxyribo-furanoside.

The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. The term "modified oligonucleotide" also encompasses oligonucleotides having at least one nucleotide with a modified base and/or sugar, such as a 2'-O-substituted, a 5'-O-substituted and/or a 3'-O-substituted ribonucleotide.

The term "nucleic acid" encompasses a genomic region or an RNA molecule transcribed therefrom. In some embodiments, the nucleic acid is mRNA.

The term "nucleotidic linkage" generally refers to a chemical linkage to join two nucleosides through their sugars (e.g. 3'-3',2'-3',2'-5',3'-5') consisting of a phosphorous atom and a charged, or neutral group (e.g., phosphodiester, phosphorothioate, phosphorodithioate or methylphosphonate) between adjacent nucleosides.

The term "oligonucleotide" refers to a polynucleoside formed from a plurality of linked nucleoside units. The nucleoside units may be part of viruses, bacteria, cell debris or oligonucleotide-based compositions (for example, siRNA and microRNA). Such oligonucleotides can also be obtained from existing nucleic acid sources, including genomic or cDNA, but are preferably produced by synthetic methods. In certain embodiments each nucleoside unit includes a heterocyclic base and a pentofuranosyl, trehalose, arabinose, 2'-deoxy-2'-substituted nucleoside, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, methylphosphonate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide-based compound" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain exemplar embodiments, these internucleoside linkages may be phosphodiester, phosphorothioate or phosphorodithioate linkages, or combinations thereof.

The term "complementary to a genomic region or an RNA molecule transcribed therefrom" is intended to mean an oligonucleotide that binds to the nucleic acid sequence under physiological conditions, for example, by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide, binding to RNA and causing pseudoknot formation. Binding by Watson-Crick or Hoogsteen base pairing under physiological conditions is measured as a practical matter by observing interference with the function of the nucleic acid sequence.

The term "peptide" generally refers to polypeptides that are of sufficient length and composition to affect a biological response, for example, antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization and methylation.

The term "pharmaceutically acceptable" means a non-toxic material that does not interfere with the effectiveness of a compound according to the invention or the biological activity of a compound according to the invention.

The term "physiologically acceptable" refers to a non-toxic material that is compatible with a biological system such as a cell, cell culture, tissue, or organism. Preferably, the biological system is a living organism, such as a mammal, particularly a human.

The term "prophylactically effective amount" generally refers to an amount sufficient to prevent or reduce the development of an undesired biological effect.

The term "therapeutically effective amount" or "pharmaceutically effective amount" generally refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful patient benefit, for example, but not limited to, healing of chronic conditions characterized by immune stimulation. Thus, a "pharmaceutically effective amount" will depend upon the context in which it is being administered. A pharmaceutically effective amount may be administered in one or more prophylactic or therapeutic administrations. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "treatment" generally refers to an approach intended to obtain a beneficial or desired result, which may include alleviation of symptoms, or delaying or ameliorating a disease progression.

In a first aspect, the invention provides antisense oligonucleotides that are complementary to a nucleic acid that is specific for human TLR3 (SEQ ID NO: 162). The antisense oligonucleotides according to the invention are optimized with respect to the targeted region of the TLR3 mRNA coding sequence, 5' untranslated region or 3' untranslated region, in their chemical modification, or both. In some embodiments of this aspect, the compounds are complementary to a region within nucleobases 102 through 2816 of the coding region, or 1-101 of the 5' untranslated region, or 2817-3057 of the 3' untranslated region of TLR3 mRNA. (SEQ ID NO: 162).

Antisense oligonucleotides according to the invention are useful in treating and/or preventing diseases wherein inhibiting a TLR3-mediated immune response would be beneficial. TLR3-targeted antisense oligonucleotides according to the invention that are useful include, but are not limited to, antisense oligonucleotides comprising naturally occurring nucleotides, modified nucleotides, modified oligonucleotides and/or backbone modified oligonucleotides. However, antisense oligonucleotides that inhibit the translation of mRNA encoded proteins may produce undesired biological effects, including but not limited to insufficiently active antisense oligonucleotides, inadequate bioavailability, suboptimal pharmacokinetics or pharmacodynamics, and immune stimulation. Thus, the optimal design of an antisense oligonucleotide according to the invention requires many considerations beyond simple design of a complementary sequence. Thus, preparation of TLR3-targeted antisense oligonucleotides according to the invention is intended to incorporate changes necessary to limit secondary structure interference with antisense activity, enhance the oligonucleotide's target specificity, minimize interaction with binding or competing factors (for example, proteins), optimize cellular uptake, stability, bioavailability, pharmacokinetics and pharmacodynamics, and/or inhibit, prevent or suppress immune cell activation. Such inhibition, prevention or suppression of immune cell activation may be accomplished in a number of ways without compromising the antisense oligonucleotide's ability to hybridize to nucleotide sequences contained within the mRNA for TLR3, including, without limitation, incorporation of one or more modified nucleotides or nucleotide linkages, wherein such modified nucleotides are a 2'-O-methyl, a 3'-O-methyl, a 5-methyl, a 2'-O-methoxyethyl-C, a 2'-O-methoxyethyl-5-methyl-C and/or a 2'-O-methyl-5-methyl-C on the "C" of a "CpG" dinucleotide, a 2'-O-substituted-G, a 2'-O-methyl-G and/or a 2'-O-methoxyethoxy-G on the "G" of the CpG, and such modified nucleotide linkages are a non-phosphate or non-phosphorothioate internucleoside linkage between the C and G of a "CpG" dinucleotide, a methylphosphonate linkage and/or a 2'-5' internucleotide linkage between the C and G of a "CpG" dinucleotide.

It has been determined that the human TLR3 coding region is comprised of approximately 2.7 kB, and the transcript corresponding to the 904 amino acid protein have also been identified in humans (Rock et al. (1998) Proc. Natl. Acad. Sci. 95:588-593). The sequence of the gene encoding TLR3 has been reported in mice (Applequist et al. (2002) Int. Immunol. 14:1065-1074) and for humans (Rock et al. (1998) Proc. Natl. Acad. Sci. 95:588-593). The oligonucleotides of the invention are directed to optimally available portions of the TLR3 nucleic acid sequence that most effectively act as a target for inhibiting TLR3 expression. These targeted regions of the TLR3 gene include portions of the known exons or 5' untranslated region. In addition, intron-exon boundaries, 3' untranslated regions and introns are potentially useful targets for antisense inhibition of TLR3 expression. The nucleotide sequences of some representative, non-limiting oligonucleotides specific for human TLR3 have SEQ ID NOS: 1-161. The nucleotide sequences of optimized oligonucleotides according to the invention include those having SEQ ID NOS: 11, 12, 18, 26, 47, 63, 78, 88, 92, 110, 114 or 144.

The oligonucleotides of the invention are at least 14 nucleotides in length, but are preferably 15 to 60 nucleotides long, preferably 20 to 50 nucleotides in length. In some embodiments, these oligonucleotides contain from about 14 to 28 nucleotides or from about 16 to 25 nucleotides or from about 18 to 22 nucleotides or 20 nucleotides. These oligonucleotides can be prepared by the art recognized methods such as phosphoramidate or H-phosphonate chemistry which can be carried out manually or by an automated synthesizer. The synthetic TLR3 antisense oligonucleotides of the invention may also be modified in a number of ways without compromising their ability to hybridize to TLR3 mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate triester, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

For example, U.S. Pat. No. 5,149,797 describes traditional chimeric oligonucleotides having a phosphorothioate core region interposed between methylphosphonate or phosphoramidate flanking regions. U.S. Pat. No. 5,652,356 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various oligonucleotides with modified internucleotide linkages can be prepared according to standard methods. Phosphorothioate linkages may be mixed Rp and Sp enantiomers, or they may be made stereoregular or substantially stereoregular in either Rp or Sp form according to standard procedures.

Oligonucleotides which are self-stabilized are also considered to be modified oligonucleotides useful in the methods of the invention (Tang et al. (1993) Nucleic Acids Res. 20:2729-2735). These oligonucleotides comprise two regions: a target hybridizing region; and a self-complementary region having an oligonucleotide sequence complementary to a nucleic acid sequence that is within the self-stabilized oligonucleotide.

Other modifications include those which are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3', 5'-substituted oligonucleotide having a sugar which, at both its 3' and 5' positions, is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O-alkyl group containing 1-6 saturated or unsaturated carbon atoms, or with an —O-aryl, or —O-allyl group having 2-6 carbon atoms wherein such —O-alkyl, —O-aryl or —O-allyl group may be unsubstituted or may be substituted, for example with halo, hydroxy, trifluoromethyl cyano, nitro acyl acyloxy, alkoxy, carboxy, carbalkoxyl or amino groups. None of these substitutions are intended to exclude the native 2'-hydroxyl group in the case of ribose or 2'1-H— in the case of deoxyribose.

The oligonucleotides according to the invention can comprise one or more ribonucleotides. For example, U.S. Pat. No. 5,652,355 discloses traditional hybrid oligonucleotides having regions of 2'-O-substituted ribonucleotides flanking a DNA core region. U.S. Pat. No. 5,652,356 discloses an "inverted" hybrid oligonucleotide which includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides. Non-limiting examples of particularly useful oligonucleotides of the invention have 2'-O-alkylated ribonucleotides at their 3', 5', or 3' and 5' termini, with at least four or five contiguous nucleotides being so modified. Non-limiting examples of 2'-O-alkylated groups include 2'-O-methyl, 2'-O-ethyl, 2'-O-propyl, 2'-O-butyls and 2'-O-ethoxy-methyl.

Other modified oligonucleotides are capped with a nuclease resistance-conferring bulky substituent at their 3' and/or 5' end(s), or have a substitution in one non-bridging oxygen per nucleotide. Such modifications can be at some or all of the internucleoside linkages, as well as at either or both ends of the oligonucleotide and/or in the interior of the molecule.

The oligonucleotides of the invention can be administered in combination with one or more antisense oligonucleotides or other nucleic acid containing compounds, which are not the same target as the antisense molecule of the invention, and which comprise an immunostimulatory motif that would activate a TLR3-mediated immune response but for the presence of the TLR3 antisense oligonucleotide according to the invention. In addition, the oligonucleotides of the invention can be administered in combination with one or more vaccines, antigens, antibodies, cytotoxic agents, allergens, antibiotics, TLR antagonists, siRNA, miRNA, antisense oligonucleotides, aptamers, peptides, proteins, gene therapy vectors, DNA vaccines, adjuvants, kinase inhibitors or co-stimulatory molecules or combinations thereof.

A non-limiting list of TLR3 antisense oligonucleotides are shown in SEQ ID NO. 1 through SEQ ID NO. 165 and Table 2 below. Optimized antisense oligonucleotides according to the invention include those having SEQ ID NOS: 11, 12, 18, 26, 47, 63, 78, 88, 92, 110, 114 or 144. In Table 2, the oligonucleotide-based TLR3 antisense compounds have all phosphorothioate (PS) linkages. Those skilled in the art will recognize, however, that phosphodiester (PO) linkages, or a mixture of PS and PO linkages can be used.

TABLE 2

| SEQ ID NO./ AS NO. | Position of Binding | Antisense Sequence Orientation is 5'-3' |
|---|---|---|
| 1 | 1 | AGACGGCACT CTCGAAAGTG |
| 2 | 21 | CAGGGAAGTG TGTGGCAAAT |
| 3 | 41 | TCCAAATCCA GACATTTCAT |
| 4 | 61 | GCCTTTCCTT TTTTCTTTAG |
| 5 | 81 | ATTCTGTTGG ATGACTGCTA |
| 6 | 101 | AAGGCAAAGT CTGTCTCATG |
| 7 | 121 | GCCCCCCCAA AAGTAGATAC |
| 8 | 141 | AGCATCCCAA AGGGCAAAAG |
| 9 | 161 | TGGTGGTGGA GGATGCACAC |
| 10 | 181 | TTCATGGCTA ACAGTGCACT |
| 11 | 193 | GCAGTCAGCA ACTTCATGGC |
| 12 | 211 | AGTCAACTTC AGGTGGCTGC |
| 13 | 221 | CGGGTACCTG AGTCAACTTC |
| 14 | 241 | TATGTTTGTG GGTAGATCAT |
| 15 | 261 | TGGGTAAGGT TCAACACTGT |
| 16 | 281 | GTAATCTTCT GAGTTGATTA |
| 17 | 301 | CCTTGTGAAG TTGGCGGCTG |
| 18 | 319 | GCTAGTTAGC TGGCTATACC |
| 19 | 341 | TGGTGTTAAA TCCTACATCC |
| 20 | 361 | TTCTGGCTCC AGTTTGAGA |
| 21 | 381 | ATGGGAAGTT TCTGGCACAA |

TABLE 2-continued

| SEQ ID NO./ AS NO. | Position of Binding | Antisense Sequence Orientation is 5'-3' |
|---|---|---|
| 22 | 401 | GGAGGTTCAA AACTTTTAAC |
| 23 | 421 | TTGAGATAGC TCATTGTGCT |
| 24 | 441 | GCAAAGGTTT TATCAGAAAG |
| 25 | 461 | CAGTCAAATT CGTGCAGAAG |
| 26 | 471 | AGATGGAGTT CAGTCAAATT |
| 27 | 481 | GTTGGACATG AGATGGAGTT |
| 28 | 501 | TTTTTAATTT TCTGGATTGA |
| 29 | 521 | TCTGCTTGAC AAAGGGATTA |
| 30 | 541 | ATCTAATGTGATTAAATTCT |
| 31 | 561 | GACAAGCCAT TATGAGACAG |
| 32 | 581 | GAGTTCCTAA TTTTGTAGAT |
| 33 | 601 | GAGATTTTCC AGCTGAACCT |
| 34 | 621 | TTTGATAATA GAAGCTCTTG |
| 35 | 641 | TTAGCGCTTG AATTTTATTG |
| 36 | 661 | GATATCCAGT TCTTCACTTT |
| 37 | 681 | TTTAAAGATG AATTGGCAAA |
| 38 | 701 | TCGATGACAA CTCTAATTTT |
| 39 | 721 | AGAAAACTCT TTAATTTGAT |
| 40 | 741 | ATTGCGTGAA AACACCCTGG |
| 41 | 761 | AGAGGCCAAA TAATCTTCCA |
| 42 | 781 | CAGCTGGACA TTGTTCAGAA |
| 43 | 801 | TTCTCTGTAA GGCTGGGACC |
| 44 | 821 | TTGCTAATTC CAAACATAGC |
| 45 | 830 | TGCTTGTGTT TGCTAATTCC |
| 46 | 841 | CAGATTCCGAATGCTTGTGT |
| 47 | 860 | GCTGGCTGTT ACTCAGAGAC |
| 48 | 881 | TTGTATTGCT GGTGGTGGAC |
| 49 | 901 | CCACTTTAGT CCCAAGAAAG |
| 50 | 921 | TCGAGCATAG TGAGATTTGT |
| 51 | 941 | TTAAGTTGTT GTAGGAAAGA |
| 52 | 961 | GGAATCGTTA CCAACCACAT |
| 53 | 981 | AGTTGTGGAA GCCAAGCAAA |
| 54 | 1001 | ACTCTAGGAA GAAATATTCT |
| 55 | 1021 | CAAATGCTGT ATATTATTAT |
| 56 | 1041 | CCGTGCAAAG AGTGAGAAAA |
| 57 | 1061 | GGTACCTCAC ATTGAAAAGC |
| 58 | 1081 | AAAAGACCGT TCAAATTCA |
| 59 | 1101 | AGGGAAATAC TTTGTTTAGT |

TABLE 2-continued

| SEQ ID NO./ AS NO. | Position of Binding | Antisense Sequence Orientation is 5'-3' |
|---|---|---|
| 60 | 1121 | CAATCTTGGG GAGTGAGGCA |
| 61 | 1141 | CCACTGAAAA GAAAAATCAT |
| 62 | 1161 | AGGTGCTCCA AACATTTTAG |
| 63 | 1172 | CTTCCATGTT AAGGTGCTCC |
| 64 | 1181 | TATCATTATC TTCCATGTTA |
| 65 | 1201 | ATTGCTTTTT ATGCCTGGAA |
| 66 | 1221 | TTTATCAATC CTGTGAACAT |
| 67 | 1241 | ATAGACTTAA GTATTTCAGG |
| 68 | 1261 | CAAACTTGTA AAGGAGTTGG |
| 69 | 1281 | GTTTCATTTG TCAAAGTTCG |
| 70 | 1301 | AATGAGCAAG TGATACAAAT |
| 71 | 1321 | GTTGAGTATG TGTAAGGGAG |
| 72 | 1341 | GAGATTTTAT TCTTGGTTAG |
| 73 | 1361 | AAGCATCACT CTCTATTTTT |
| 74 | 1381 | TAGGTGGCCC AACCAAGAGA |
| 75 | 1401 | AGGCCCAGGT CAAGTACTTC |
| 76 | 1421 | GTTCTTGCCC AATTTCATTA |
| 77 | 1441 | TCTCCATTCC TGGCCTGTGA |
| 78 | 1447 | TAGACCTCTC CATTCCTGGC |
| 79 | 1461 | TCGAAAATAT TTTCTAGACC |
| 80 | 1481 | TGTTGTAGGA AAGATAGATT |
| 81 | 1501 | CCTAGTCAGC TGCAGGTACT |
| 82 | 1521 | GGGACCAAGG CAAAGGAGTT |
| 83 | 1541 | GCATCAGTCG TTGAAGGCTT |
| 84 | 1561 | TTTAAGGGCC ACCCTTCGGA |
| 85 | 1581 | GAAGGAGAGC TATCCACATT |
| 86 | 1601 | TACGAAGAGG CTGGAATGGT |
| 87 | 1621 | TAGATCCAGA ATGGTCAAGT |
| 88 | 1642 | GTTGGCTATG TTGTTGTTGC |
| 89 | 1661 | CCAACATGTC ATCATTTATG |
| 90 | 1681 | TTCTAGTTTC TCAAGACCCT |
| 91 | 1701 | TTATGCTGCA AATCGAGAAT |
| 92 | 1712 | GTGCTAAGTT GTTATGCTGC |
| 93 | 1721 | TCCAGAGCCG TGCTAAGTTG |
| 94 | 1741 | ACCACCAGGG TTTGCGTGTT |
| 95 | 1761 | CCCTTTAGGA AATAAATGGG |
| 96 | 1781 | GGATGTGGAC GTGAGACAGA |
| 97 | 1801 | GCCGTTGGAC TCCAAGTTAA |
| 98 | 1821 | TCAACTGGGA TCTCGTCAAA |
| 99 | 1841 | CAAATAAATC CTTGAAGACC |
| 100 | 1861 | TAAATCGATG ATCTTTAGTT |
| 101 | 1881 | GTGTTTAAAT TATTCAATCC |
| 102 | 1901 | TAAAGACAGA TGCTGGAAGT |
| 103 | 1921 | CTTTAGAGAC ACCTGATTAT |
| 104 | 1941 | TTCTTCTGAA GGTTCAATGA |
| 105 | 1961 | TCTCAACGGA TGTTATGAGA |
| 106 | 1981 | AGCTGGCCCG AAAACCTTCT |
| 107 | 2001 | AACTCAGTCA GGTTCCTGAA |
| 108 | 2021 | AGGGATTAAA GCGCATATCT |
| 109 | 2041 | ACTTTCACAC GTGCAATCAA |
| 110 | 2051 | ACCAGGCAAT ACTTTCACAC |
| 111 | 2061 | CAATTAACAA ACCAGGCAAT |
| 112 | 2081 | TGGTATGGGT CTCGTTAATC |
| 113 | 2101 | GCTTGACAGC TCAGGGATGT |
| 114 | 2111 | AAAGGTAGTG GCTTGACAGC |
| 115 | 2121 | GGAGTGTTGC AAAGGTAGTG |
| 116 | 2141 | GGAACCCATG ATAGTGAGGT |
| 117 | 2161 | TGTATCAAAA AGTCTCACTG |
| 118 | 2181 | GCACTGTCTT TGCAAGATGA |
| 119 | 2201 | TGAAAAGAG TTCAAAGGGG |
| 120 | 2221 | CAGGATACTG GTATTGATCA |
| 121 | 2241 | ACAATAAAGA TAAAAATCAA |
| 122 | 2261 | CCTCAAAGTG GATGAGAAGT |
| 123 | 2281 | ATAAAAGAT ATCCTCCAGC |
| 124 | 2301 | CGATGTACTG AAACATTCCA |
| 125 | 2321 | TTTCTTTGAA ACCAAGAACT |
| 126 | 2341 | CTGTTCTGTC TGTCTGTCTA |
| 127 | 2361 | ATATATGCTG CATATTCAAA |
| 128 | 2381 | TATCTTTATA GGCATGAATT |
| 129 | 2401 | ATGTTCCCAG ACCCAATCCT |
| 130 | 2421 | TCCTTTTCCA TTGAAGAGAA |
| 131 | 2441 | AAAATTTGAG AGATTGGTCT |
| 132 | 2461 | AAAGTCCCTT TCTTCCAGAC |
| 133 | 2481 | AGTTCAAAAA CACCCGCCTC |
| 134 | 2501 | TGCTGTTAAC AATTGCTTCT |
| 135 | 2521 | AATTTTTCTG CTTCTTTTGA |
| 136 | 2541 | TGGTGTGTTA TAACAAAAAT |

TABLE 2-continued

| SEQ ID NO./ AS NO. | Position of Binding | Antisense Sequence Orientation is 5'-3' |
|---|---|---|
| 137 | 2561 | ATAATGGGTC TTTTAATAGA |
| 138 | 2581 | ATGTACCTTG AATCTTTTGC |
| 139 | 2601 | ATAGCTTGTT GAACTGCATG |
| 140 | 2621 | TGGAATCCAG ATTTTGTTCA |
| 141 | 2641 | CTCAAGGAAA ACCAATATAA |
| 142 | 2661 | AGTTTATAAT CTGGAATCTC |
| 143 | 2681 | GCAAACAGAG TGCATGGTTC |
| 144 | 2688 | <u>CCTC</u>TTCGCA AACAGA<u>GTGC</u> |
| 145 | 2701 | AGATTTAAAC ATTCCTCTTC |
| 146 | 2721 | GGCCAGTTCA AGATGCAGTG |
| 147 | 2741 | CTATCCGTTC TTTCTGAACT |
| 148 | 2761 | CAATTTATGA CGAAAGGCAC |
| 149 | 2781 | TTGGATCCAA GTGCTACTTG |
| 150 | 2801 | AAATTTAATG TACAGAGTTT |
| 151 | 2821 | TGCTAATTGA ATATTTAAAT |
| 152 | 2841 | AATTGAGAAA GTTTCTCCTT |
| 153 | 2861 | ATTTGCCATA GAACTTTTA |
| 154 | 2881 | CACCTTTATG GAAAACTTAA |
| 155 | 2901 | TATGAATAAA CAAATTATAA |
| 156 | 2921 | AGAATATAAT CATTTACAAA |
| 157 | 2941 | AGAAGAGATG TAATTGTGAT |
| 158 | 2961 | ATAAGGAGAC ACATTTTCCT |
| 159 | 2981 | TTGTCAAAAA TAGGCCTGAA |
| 160 | 3001 | TTTGGGTAAA ATTAAGTCAA |
| 161 | 3021 | TACGTGCTTA TATGTTTTAT |
| 163 | 556 (mouse) | 5'-<u>GCAG</u>TTCTTGGAGGTT<u>CTCC</u>-3' (MOUSE) |
| 164 | 1392 (mouse) | 5'-<u>CAGA</u>CCTCTCCATTCC<u>TGGC</u>-3' (MOUSE) |
| 165 | 1891 (mouse) | 5'-<u>TGAG</u>GTTCTTCTGGAG<u>GTTC</u>-3' (MOUSE) |
| 166 | 2551 (mouse) | 5'-<u>GCTC</u>AATAGCTTGCTG<u>AACT</u>-3' (MOUSE) |

AS means antisense. Underlined nucleotides are 2'-O-methylribonucleotides; all others are 2'-deoxyribonucleotides. In the exemplar antisense oligonucleotides according to the invention, when a "CG" dinucleotide is contained in the sequence, such oligonucleotide is modified to remove or prevent the immune stimulatory properties of the oligonucleotide.

In a second aspect, the invention provides a composition comprising at least one optimized antisense oligonucleotide according to the invention and a physiologically acceptable carrier, diluent or excipient. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of TLR3 expression. For example, combinations of synthetic oligonucleotides, each of which is directed to different regions of the TLR3 mRNA, may be used in the pharmaceutical compositions of the invention. The pharmaceutical composition of the-invention may further contain nucleotide analogs such as azidothymidine, dideoxycytidine, dideoxyinosine, and the like. Such additional factors and/or agents may be included in the pharmaceutical composition to produce a synergistic, additive or enhanced effect with the synthetic oligonucleotide of the invention, or to minimize side-effects caused by the synthetic oligonucleotide of the invention. The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. Nos. 4,235,871; 4,501,728; 4,837,028; and 4,737,323. The pharmaceutical composition of the invention may further include compounds such as cyclodextrins and the like that enhance delivery of oligonucleotides into cells or slow release polymers.

In a third aspect, the invention provides a method of inhibiting TLR3 expression. In this method, an oligonucleotide or multiple oligonucleotides of the invention are specifically contacted or hybridized with TLR3 mRNA either in vitro or in a cell.

In a fourth aspect, the invention provides methods for inhibiting the expression of TLR3 in a mammal, particularly a human, such methods comprising administering to the mammal a compound or composition according to the invention.

In a fifth aspect, the invention provides a method for inhibiting a TLR-mediated immune response in a mammal, the method comprising administering to the mammal a TLR3 antisense oligonucleotide according to the invention in a pharmaceutically effective amount, wherein routes of administration include, but are not limited to, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

In a sixth aspect, the invention provides a method for therapeutically treating a mammal having a disease mediated by TLR3, such method comprising administering to the mammal, particularly a human, a TLR3 antisense oligonucleotide of the invention in a pharmaceutically effective amount.

In certain embodiments, the disease is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. In certain embodiments, inflammatory disorders include without limitation airway inflammation, asthma, autoimmune diseases, chronic inflammation, chronic prostatitis, glomerulonephritis, Behçcet's disease, hypersensitivities, inflammatory bowel disease, reperfusion injury, rheumatoid arthritis, transplant rejection, ulcerative colitis, uveitis, conjunctivitis and vasculitis.

In a seventh aspect, the invention provides methods for preventing a disease or disorder in a mammal, particularly a human, at risk of contracting or developing a disease or disorder mediated by TLR3. The method according to this aspect comprises administering to the mammal a prophylactically effective amount of an antisense oligonucleotide or composition according to the invention. Such diseases and disorders include, without limitation, cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen in a vertebrate. Autoimmune disorders include, without limitation, lupus erythematosus, multiple sclerosis, type I diabetes mellitus, irritable bowel syndrome, Chron's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barré syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjögren's syndrome, temporal arteritis ("giant cell arteritis"), vasculitis, vitiligo, vulvodynia and Wegener's granulomatosis. Inflammatory disorders include, without limitation, airway inflammation, asthma, autoimmune diseases, chronic inflammation, chronic prostatitis, glomerulonephritis, Behçcet's disease, hypersensitivities, inflammatory bowel disease, reperfusion injury, rheumatoid arthritis, transplant rejection, ulcerative colitis, uveitis, conjunctivitis and vasculitis.

In an eighth aspect of the invention, the invention provides methods for down-regulating TLR3 expression and thus preventing the "off-target" activity of dsRNA molecules, or other compounds or drugs that have a side effect of activating TLR3. Certain dsRNA-containing compounds that are designed to down-regulate expression of targets other than TLR3 also are recognized by TLR3 proteins and induce an immune response. This activity can be referred to as "off-target" effects. The TLR3 antisense oligonucleotides according to the invention have the ability to down-regulate TLR3 expression and thus prevent the TLR3-mediated off-target activity of the non-TLR3 targeted dsRNA molecules. For example, the TLR3 antisense oligonucleotide according to the invention can be administered in combination with one or more dsRNA oligonucleotides, which are not targeted to the same molecule as the antisense oligonucleotides of the invention, and which comprise an immunostimulatory motif that would activate a TLR3-mediate immune response but for the presence the TLR3 antisense oligonucleotide according to the invention.

In a ninth aspect, the invention provides a method for inhibiting TLR3 expression and activity in a mammal, comprising administering to the mammal an antisense oligonucleotide complementary to TLR3 mRNA and an antagonist of TLR3 protein, a kinase inhibitor or an inhibitor of STAT (signal transduction and transcription) protein. According to this aspect, TLR3 expression is inhibited by the antisense oligonucleotide, while any TLR3 protein residually expressed is inhibited by the antagonist. Preferred antagonists include anti-TLR3 antibodies or binding fragments or peptidomimetics thereof, RNA-based compounds, oligonucleotide-based compounds, and/or small molecule inhibitors of TLR3 activity or of a signaling protein's activity.

In the various methods according to the invention, a therapeutically or prophylactically effective amount of a synthetic oligonucleotide of the invention and effective in inhibiting the expression of TLR3 is administered to a cell. This cell may be part of a cell culture, a neovascularized tissue culture, or may be part or the whole body of a mammal such as a human or other mammal. Administration of the therapeutic compositions of TLR3 antisense oligonucleotide can be carried out using known procedures at dosages and for periods of time effective to reduce symptoms or surrogate markers of the disease, depending on the condition and response, as determined by those with skill in the art. It may be desirable to administer simultaneously, or sequentially a therapeutically effective amount of one or more of the therapeutic TLR3 antisense oligonucleotides of the invention to an individual as a single treatment episode. In some exemplar embodiments of the methods of the invention described above, the oligonucleotide is administered locally and/or systemically. The term "administered locally" refers to delivery to a defined area or region of the body, while the term "systemic administration" is meant to encompass delivery to the whole organism.

In any of the methods according to the invention, one or more of the TLR3 antisense oligonucleotide can be administered alone or in combination with any other agent useful for treating the disease or condition that does not diminish the immune modulatory effect of the TLR3 antisense oligonucleotide. In any of the methods according to the invention, the agent useful for treating the disease or condition includes, but is not limited to, one or more vaccines, antigens, antibodies, cytotoxic agents, allergens, antibiotics, antisense oligonucleotides, TLR agonist, TLR antagonist, siRNA, miRNA, peptides, proteins, gene therapy vectors, DNA vaccines, adjuvants or kinase inhibitors to enhance the specificity or magnitude of the immune response, or co-stimulatory molecules such as cytokines, chemokines, protein ligands, trans-activating factors, peptides and peptides comprising modified amino acids. For example, in the treatment of autoimmune disease, it is contemplated that the TLR3 antisense oligonucleotide may be administered in combination with one or more targeted therapeutic agents and/or monoclonal antibodies. Alternatively, the agent can include DNA vectors encoding for antigen or allergen. In these embodiments, the TLR3 antisense oligonucleotide of the invention can produce direct immune modulatory or suppressive effects. When co-administered with one or more other therapies, the synthetic oligonucleotide of the invention may be administered either simultaneously with the other treatment(s), or sequentially.

In the various methods according to the invention the route of administration may be, without limitation, parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution or glycols such as ethylene glycol, propylene glycol or polyethylene glycol. When administered in liquid form, the pharmaceutical composition contains from about 0.5 to 90% by weight of the synthetic oligonucleotide or from about 1 to 50% synthetic oligonucleotide.

When a therapeutically effective amount of synthetic oligonucleotide of the invention is administered by parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, the synthetic antisense oligonucleotide will be in the form of a pyrogen-free, parenterally acceptable aqueous solution. The preparation of such parenterally acceptable solutions, having due regard to pH, isotonicity, stability, and the like, is within the skill in the art. A pharmaceutical composition for parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection or other vehicle as known in the art. The pharmaceutical composition of the present invention may also contain stabilizers, preservatives, buffers, antioxidants or other additives known to those of skill in the art.

When administered parenteral, mucosal delivery, oral, sublingual, transdermal, topical, inhalation, intranasal, aerosol, intraocular, intratracheal, intrarectal, vaginal, by gene gun, dermal patch or in eye drop or mouthwash form, doses ranging from 0.01% to 10% (weight/volume) may be used. When administered in liquid form, a liquid carrier such as water, petroleum, oils of animal or plant origin such as peanut oil, mineral oil, soybean oil, sesame oil or synthetic oils may be added. Topical administration may be by liposome or transdermal time-release patch.

The amount of synthetic oligonucleotide in the pharmaceutical composition of the present invention will depend upon the nature and severity of the condition being treated, and on the nature of prior treatments which the patent has undergone. It is contemplated that the various pharmaceutical compositions used to practice the method of the present invention should contain about 10 micrograms to about 20 mg of synthetic oligonucleotide per kg body or organ weight.

The duration of intravenous therapy using the pharmaceutical composition of the present invention will vary, depending on the severity of the disease being treated and the condition and potential idiosyncratic response of each individual patient.

Some diseases lend themselves to acute treatment while others require longer term therapy. Both acute and long term intervention in diseases are worthy goals. Injections of antisense oligonucleotides against TLR3 can be an effective means of inhibiting certain diseases in an acute situation. However for long term therapy over a period of weeks, months or years, systemic delivery (intraperitoneal, intramuscular, subcutaneous, intravenous) either with carriers such as saline, slow release polymers or liposomes are likely to be considered.

In some chronic diseases, systemic administration of oligonucleotides may be preferable. The frequency of injections is from continuous infusion to once a month, several times per month or less frequently will be determined based on the disease process and the biological half life of the oligonucleotides.

The oligonucleotides and methods of the invention are also useful for examining the function of the TLR3 gene in a cell or in a control mammal or in a mammal afflicted with a disease associated with TLR3 or immune stimulation through TLR3. In such use, the cell or mammal is administered the oligonucleotide, and the expression of TLR3 mRNA or protein is examined.

Without being limited to any theory or mechanism, it is generally believed that the activity of oligonucleotides according to the invention depends on the hybridization of the oligonucleotide to the target nucleic acid (e.g. to at least a portion of a genomic region, gene or mRNA transcript thereof), thus disrupting the function of the target. Such hybridization under physiological conditions is measured as a practical matter by observing interference with the function of the nucleic acid sequence. Thus, an exemplar oligonucleotide used in accordance with the invention is capable of forming a stable duplex (or triplex in the Hoogsteen or other hydrogen bond pairing mechanism) with the target nucleic acid; activating RNase H or other in vivo enzymes thereby causing effective destruction of the target RNA molecule; and is capable of resisting nucleolytic degradation (e.g. endonuclease and exonuclease activity) in vivo. A number of the modifications to oligonucleotides described above and others which are known in the art specifically and successfully address each of these exemplar characteristics.

The following examples illustrate the exemplar modes of making and practicing the present invention, but are not meant to limit the scope of the invention since alternative methods may be utilized to obtain similar results.

EXAMPLE 1

Preparation of TLR3-Specific Antisense Oligonucleotides

Chemical entities according to the invention were synthesized on a 1 μmol to 0.1 mM scale using an automated DNA synthesizer (OligoPilot II, AKTA, (Amersham) and/or Expedite 8909 (Applied Biosystem)), following the linear synthesis procedure outlined in FIG. 1.

5'-DMT dA, dG, dC and T phosphoramidites were purchased from Proligo (Boulder, Colo.). 5'-DMT 7-deaza-dG and araG phosphoramidites were obtained from Chemgenes (Wilmington, Mass.). DiDMT-glycerol linker solid support was obtained from Chemgenes. 1-(2'-deoxy-β-D-ribofuranosyl)-2-oxo-7-deaza-8-methyl-purine amidite was obtained from Glen Research (Sterling, Va.), 2'-O-methylribonuncleoside amidites were obtained from Promega (Obispo, Calif.). All compounds according to the invention were phosphorothioate backbone modified.

All nucleoside phosphoramidites were characterized by $^{31}$P and $^{1}$H NMR spectra. Modified nucleosides were incorporated at specific sites using normal coupling cycles recommended by the supplier. After synthesis, compounds were deprotected using concentrated ammonium hydroxide and purified by reverse phase HPLC, detritylation, followed by dialysis. Purified compounds as sodium salt form were lyophilized prior to use. Purity was tested by CGE and MALDI-TOF MS. Endotoxin levels were determined by LAL test and were below 1.0 EU/mg.

EXAMPLE 2

Cell Culture Conditions and Reagents

HEK293 Cell Culture Assays for TLR3 Antisense Activity

HEK293 XL cells stably expressing human TLR3 (Invivogen, San Diego, Calif.) were plated in 48-well plates in 250 µL/well DMEM supplemented with 10% heat-inactivated FBS in a 5% CO2 incubator. At 80% confluence, cultures were transiently transfected with 400 ng/mL of the secreted form of human embryonic alkaline phosphatase (SEAP) reporter plasmid (pNifty2-Seap) (Invivogen) in the presence of 4 µL/mL of lipofectamine (Invitrogen, Carlsbad, Calif.) in culture medium. Plasmid DNA and lipofectamine were diluted separately in serum-free medium and incubated at room temperature for 5 min. After incubation, the diluted DNA and lipofectamine were mixed and the mixtures were incubated further at room temperature for 20 min. Aliquots of 25 µL of the DNA/lipofectamine mixture containing 100 ng of plasmid DNA and 1 µL of lipofectamine were added to each well of the cell culture plate, and the cells were transfected for 6 h. After transfection, medium was replaced with fresh culture medium (no antibiotics), antisense compounds were added to the wells, and incubation continued for 18-20 h. Cells were then stimulated with the TLR3 agonist for 24 h.

At the end of the treatment, 20 µL of culture supernatant was taken from each well and assayed for SEAP assay by the Quanti Blue method according to the manufacturer's protocol (Invivogen). The data are shown as fold increase in NF-κB activity over PBS control.

EXAMPLE 3

In vivo Activity of TLR3 Antisense Oligonucleotide

Female C57BL/6 mice of 5-6 weeks age (N=3/group) were injected with exemplar murine TLR3 antisense oligonucleotides according to the invention at 5 mg/kg, or PBS, subcutaneously once a day for three days. Subsequent to administration of the TLR3 antisense oligonucleotide, mice were injected with 0.25 mg/kg of a TLR3 agonist subcutaneously. Two hours after administration of the TLR3 agonist, blood was collected and IL-12 concentration was determined by ELISA.

Equivalents

Those skilled in the art will recognize, or be able to ascertain, using no more than routine experimentation, numerous equivalents to the specific substances and procedures described herein. For example, antisense oligonucleotides that overlap with the oligonucleotides may be used. Such equivalents are considered to be within the scope of this invention, and are covered by the following claims.

What is claimed is:

1. A synthetic antisense oligonucleotide targeted to TLR3 mRNA (SEQ ID NO: 162), wherein the antisense oligonucleotide has a sequence consisting of SEQ ID NOs: 11, 12, 18, 26, 47, 63, 78, 88, 92, 110, 114 or 144, and wherein the oligonucleotide specifically hybridizes to and inhibits the expression of human TLR3.

2. A composition comprising a synthetic antisense oligonucleotide according to claim 1 and a physiologically acceptable carrier.

3. A method for inhibiting the expression of TLR3, the method comprising administering a synthetic antisense oligonucleotide according to claim 1.

4. A method for inhibiting the expression of TLR3, the method comprising administering a composition according to claim 2.

5. A method for inhibiting the expression of TLR3 in a mammal, the method comprising administering to the mammal a synthetic antisense oligonucleotide according to claim 1.

6. A method for inhibiting the expression of TLR3 in a mammal, the method comprising administering to the mammal a composition according to claim 2.

7. A method for inhibiting a TLR3-mediated immune response in a mammal, the method comprising administering to the mammal a synthetic antisense oligonucleotide according to claim 1 in a pharmaceutically effective amount.

8. A method for inhibiting a TLR3-mediated immune response in a mammal, the method comprising administering to the mammal a composition according to claim 2 in a pharmaceutically effective amount.

9. A method for down-regulating TLR3 expression and thus preventing undesired TLR3-mediated immune stimulation by a compound that activates TLR3, the method comprising administering a synthetic antisense oligonucleotide according to claim 1 in combination with one or more compounds which comprise an immunostimulatory motif that would activate a TLR3-mediated immune response but for the presence the antisense oligonucleotide.

10. A method for down-regulating TLR3 expression and thus preventing undesired TLR3-mediated immune stimulation by a compound that activates TLR3, the method comprising administering a composition according to claim 2 in combination with one or more compounds which comprise an immunostimulatory motif that would activate a TLR3-mediated immune response but for the presence of the composition.

11. The method according to claim 5, wherein the mammal is a human.

12. The method according to claim 9, wherein the compound is one or more non-TLR3 antisense oligonucleotides comprising an immunostimulatory motif that would otherwise activate a TLR3-mediated immune response.

13. The method according to claim 3, comprising further administering one or more vaccines, antigens, antibodies, cytotoxic agents, allergens, antibiotics, antisense oligonucleotides, TLR agonist, TLR antagonist, siRNA, miRNA, antisense oligonucleotides, aptamers, proteins, gene therapy vectors, DNA vaccines, adjuvants, costimulatory molecules or combinations thereof 14. A method for inhibiting TLR3 expression and activity in a mammal, comprising administering to the mammal an antisense oligonucleotide according to claim 1 and an antagonist of TLR3 protein.

15. The method according to claim 14, wherein the TLR3 protein antagonist is selected from the group consisting of anti-TLR 3 antibodies or binding fragments or peptidomimetics thereof, RNA-based compounds, oligonucleotide-based compounds, and small molecule inhibitors of TLR3 activity.

16. The synthetic antisense oligonucleotide according to claim 1, wherein the antisense oligonucleotide has a sequence consisting of SEQ ID NO: 11.

17. The synthetic antisense oligonucleotide according to claim 1, wherein the antisense oligonucleotide has a sequence consisting of SEQ ID NO: 12.

18. The synthetic antisense oligonucleotide according to claim 1, wherein the antisense oligonucleotide has a sequence consisting of SEQ ID NO: 18.

19. The synthetic antisense oligonucleotide according to claim 1, wherein the antisense oligonucleotide has a sequence consisting of SEQ ID NO: 26.

20. The synthetic antisense oligonucleotide according to claim 1, wherein the antisense oligonucleotide has a sequence consisting of SEQ ID NO: 47.

21. The synthetic antisense oligonucleotide according to claim 1, wherein the antisense oligonucleotide has a sequence consisting of SEQ ID NO: 63.

22. The synthetic antisense oligonucleotide according to claim 1, wherein the antisense oligonucleotide has a sequence consisting of SEQ ID NO: 78.

23. The synthetic antisense oligonucleotide according to claim 1, wherein the antisense oligonucleotide has a sequence consisting of SEQ ID NO: 88.

24. The synthetic antisense oligonucleotide according to claim 1, wherein the antisense oligonucleotide has a sequence consisting of SEQ ID NO: 92.

25. The synthetic antisense oligonucleotide according to claim 1, wherein the antisense oligonucleotide has a sequence consisting of SEQ ID NO: 110.

26. The synthetic antisense oligonucleotide according to claim 1, wherein the antisense oligonucleotide has a sequence consisting of SEQ ID NO: 114.

27. The synthetic antisense oligonucleotide according to claim 1, wherein the antisense oligonucleotide has a sequence consisting of SEQ ID NO: 144.

28. A combination comprising the synthetic antisense oligonucleotide according to claim 1 and a TLR3 antagonist.

29. A combination comprising the synthetic antisense oligonucleotide according to claim 1 and a kinase inhibitor.

30. A combination comprising the synthetic antisense oligonucleotide according to claim 1 and an inhibitor of STAT protein.

* * * * *

SEQUENCE LISTING

```
<160> NUMBER OF SEQ ID NOS: 166

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
agacggcact ctcgaaagtg                                          20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
cagggaagtg tgtggcaaat                                          20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 3
tccaaatcca gacatttcat                                              20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
gcctttcctt ttttctttag                                              20

<210> SEQ ID NO 5
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 5
attctgttgg atgactgcta                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 6
aaggcaaagt ctgtctcatg                                              20

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
gcccccccaa aagtagatac                                              20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
agcatcccaa agggcaaaag                                              20

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
tggtggtgga ggatgcacac                                              20

<210> SEQ ID NO 10
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 10
ttcatggcta acagtgcact                                              20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 11
gcagtcagca acttcatggc                                              20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 12
agtcaacttc aggtggctgc                                              20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
cgggtacctg agtcaacttc                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
tatgtttgtg ggtagatcat                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 15
tgggtaaggt tcaacactgt                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
gtaatcttct gagttgatta                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ccttgtgaag ttggcggctg                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 18
gctagttagc tggctatacc                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tggtgttaaa tcctacatcc                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ttctggctcc agttttgaga                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 21
atgggaagtt tctggcacaa                                                                 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ggaggttcaa aactttaac                                                                  20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ttgagatagc tcattgtgct                                                                 20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
gcaaaggttt tatcagaaag                                                                 20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
cagtcaaatt cgtgcagaag                                                                 20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 26
agatggagtt cagtcaaatt                                                                 20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 27
gttggacatg agatggagtt                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tttttaattt tctggattga                                          20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tctgcttgac aaagggatta                                          20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
atctaatgtg attaaattct                                          20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gacaagccat tatgagacag                                          20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gagttcctaa ttttgtagat                                          20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gagattttcc agctgaacct                                          20

<210> SEQ ID NO 34
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 34
tttgataata gaagctcttg                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ttagcgcttg aattttattg                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gatatccagt tcttcacttt                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tttaaagatg aattggcaaa                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tcgatgacaa ctctaatttt                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
agaaaactct ttaatttgat                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
attgcgtgaa aacaccctgg                                               20
```

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
agaggccaaa taatcttcca                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cagctggaca ttgttcagaa                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ttctctgtaa ggctgggacc                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ttgctaattc caaacatagc                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tgcttgtgtt tgctaattcc                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cagattccga atgcttgtgt                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

```
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 47
gctggctgtt actcagagac                                                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttgtattgct ggtggtggac                                                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ccactttagt cccaagaaag                                                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tcgagcatag tgagatttgt                                                    20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ttaagttgtt gtaggaaaga                                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ggaatcgtta ccaaccacat                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 53
agttgtggaa gccaagcaaa                                           20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
actctaggaa gaaatattct                                           20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
caaatgctgt atattattat                                           20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ccgtgcaaag agtgagaaaa                                           20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ggtacctcac attgaaaagc                                           20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
aaaagaccgt ttcaaattca                                           20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
agggaaatac tttgtttagt                                           20

<210> SEQ ID NO 60
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 60
caatcttggg gagtgaggca                                                 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ccactgaaaa gaaaaatcat                                                 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
aggtgctcca aacattttag                                                 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 63
cttccatgtt aaggtgctcc                                                 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tatcattatc ttccatgtta                                                 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
attgcttttt atgcctggaa                                                 20

<210> SEQ ID NO 66
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 66
tttatcaatc ctgtgaacat                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
atagacttaa gtatttcagg                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
caaacttgta aaggagttgg                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gtttcatttg tcaaagttcg                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
aatgagcaag tgatacaaat                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gttgagtatg tgtaagggag                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gagattttat tcttggttag                                              20
```

```
<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
aagcatcact ctctattttt                                             20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
taggtggccc aaccaagaga                                             20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
aggcccaggt caagtacttc                                             20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gttcttgccc aatttcatta                                             20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tctccattcc tggcctgtga                                             20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 78
tagacctctc cattcctggc                                             20
```

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tcgaaaatat tttctagacc                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tgttgtagga aagatagatt                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
cctagtcagc tgcaggtact                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gggaccaagg caaaggagtt                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gcatcagtcg ttgaaggctt                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tttaagggcc acccttcgga                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 85
gaaggagagc tatccacatt                                          20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tacgaagagg ctggaatggt                                          20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tagatccaga atggtcaagt                                          20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 88
gttggctatg ttgttgttgc                                          20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ccaacatgtc atcatttatg                                          20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ttctagtttc tcaagaccct                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 91
ttatgctgca aatcgagaat                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 92
gtgctaagtt gttatgctgc                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tccagagccg tgctaagttg                                               20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
accaccaggg tttgcgtgtt                                               20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
ccctttagga aataaatggg                                               20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
ggatgtggag gtgagacaga                                               20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 97
gccgttggac tccaagttaa                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
tcaactggga tctcgtcaaa                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
caaataaatc cttgaagacc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
taaatcgatg atctttagtt                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gtgtttaaat tattcaatcc                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
taaagacaga tgctggaagt                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
ctttagagac acctgattat                                              20

<210> SEQ ID NO 104
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 104
ttcttctgaa ggttcaatga                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
tctcaacgga tgttatgaga                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
agctggcccg aaaaccttct                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
aactcagtca ggttcctgaa                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
agggattaaa gcgcatatct                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
actttcacac gtgcaatcaa                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
```

```
<220> FEATURE:
<221> NAME/KEY: modified_base
<222> LOCATION: (17)..(20)
<223> OTHER INFORMATION: 2'-OMe

<400> SEQUENCE: 110
accaggcaat actttcacac                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
caattaacaa accaggcaat                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
tggtatgggt ctcgttaatc                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
gcttgacagc tcagggatgt                                               20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 114
aaaggtagtg gcttgacagc                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
ggagtgttgc aaaggtagtg                                               20

<210> SEQ ID NO 116
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 116
ggaacccatg atagtgaggt                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
tgtatcaaaa agtctcactg                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
gcactgtctt tgcaagatga                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
tgaaaaagag ttcaaagggg                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
caggatactg gtattgatca                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
acaataaaga taaaaatcaa                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
cctcaaagtg gatgagaagt                                              20
```

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
ataaaaagat atcctccagc                                               20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
cgatgtactg aaacattcca                                               20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tttctttgaa accaagaact                                               20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
ctgttctgtc tgtctgtcta                                               20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
atatatgctg catattcaaa                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
tatctttata ggcatgaatt                                               20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 129
atgttcccag acccaatcct                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tcctttccca ttgaagagaa                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
aaaatttgag agattggtct                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
aaagtccctt tcttccagac                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
agttcaaaaa cacccgcctc                                              20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
tgctgttaac aattgcttct                                              20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
aatttttctg cttcttttga                                              20

<210> SEQ ID NO 136
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 136
tggtgtgtta taacaaaaat                                                  20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ataatgggtc ttttaataga                                                  20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
atgtaccttg aatcttttgc                                                  20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
atagcttgtt gaactgcatg                                                  20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
tggaatccag attttgttca                                                  20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
ctcaaggaaa accaatataa                                                  20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
agtttataat ctggaatctc                                                  20
```

```
<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
gcaaacagag tgcatggttc                                                 20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 144
cctcttcgca aacagagtgc                                                 20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
agatttaaac attcctcttc                                                 20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
ggccagttca agatgcagtg                                                 20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
ctatccgttc tttctgaact                                                 20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
caatttatga cgaaaggcac                                                 20
```

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
ttggatccaa gtgctacttg                                           20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
aaatttaatg tacagagttt                                           20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
tgctaattga atatttaaat                                           20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
aattgagaaa gtttctcctt                                           20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
atttgccata gaactttta                                            20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
cacctttatg gaaaacttaa                                           20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 155
tatgaataaa caaattataa                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agaatataat catttacaaa                                              20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
agaagagatg taattgtgat                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ataaggagac acattttcct                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ttgtcaaaaa taggcctgaa                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tttgggtaaa attaagtcaa                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
tacgtgctta tatgttttat                                              20

<210> SEQ ID NO 162
<211> LENGTH: 3057
```

<212> TYPE: DNA
<213> ORGANISM: Artificial Sequence
<220> FEATURE:
<223> OTHER INFORMATION: Antisense Oligonucleotide

<400> SEQUENCE: 162

| | | | | | |
|---|---|---|---|---|---|
| cactttcgag | agtgccgtct | atttgccaca | cacttccctg | atgaaatgtc | tggatttgga | 60 |
| ctaaagaaaa | aaggaaaggc | tagcagtcat | ccaacagaat | catgagacag | actttgcctt | 120 |
| gtatctactt | ttggggggc | cttttgccct | ttgggatgct | gtgtgcatcc | tccaccacca | 180 |
| agtgcactgt | tagccatgaa | gttgctgact | gcagccacct | gaagttgact | caggtacccg | 240 |
| atgatctacc | cacaaacata | acagtgttga | accttaccca | taatcaactc | agaagattac | 300 |
| cagccgccaa | cttcacaagg | tatagccagc | taactagctt | ggatgtagga | tttaacacca | 360 |
| tctcaaaact | ggagccagaa | ttgtgccaga | aacttcccat | gttaaaagtt | ttgaacctcc | 420 |
| agcacaatga | gctatctcaa | ctttctgata | aaacctttgc | cttctgcacg | aatttgactg | 480 |
| aactccatct | catgtccaac | tcaatccaga | aaattaaaaa | taatcccttt | gtcaagcaga | 540 |
| agaatttaat | cacattagat | ctgtctcata | atggcttgtc | atctacaaaa | ttaggaactc | 600 |
| aggttcagct | ggaaaatctc | caagagcttc | tattatcaaa | caataaaatt | caagcgctaa | 660 |
| aaagtgaaga | actggatatc | tttgccaatt | catctttaaa | aaaattagag | ttgtcatcga | 720 |
| atcaaattaa | agagttttct | ccagggtgtt | ttcacgcaat | tggaagatta | tttggcctct | 780 |
| ttctgaacaa | tgtccagctg | ggtcccagcc | ttacagagaa | gctatgtttg | gaattagcaa | 840 |
| acacaagcat | tcggaatctg | tctctgagta | acagccagct | gtccaccacc | agcaatacaa | 900 |
| ctttcttggg | actaaagtgg | acaaatctca | ctatgctcga | tctttcctac | aacaacttaa | 960 |
| atgtggttgg | taacgattcc | tttgcttggc | ttccacaact | agaatatttc | ttcctagagt | 1020 |
| ataataatat | acagcatttg | ttttctcact | ctttgcacgg | gcttttcaat | gtgaggtacc | 1080 |
| tgaatttgaa | acgtctttt | actaaacaaa | gtatttccct | tgcctcactc | cccaagattg | 1140 |
| atgattttc | ttttcagtgg | ctaaaatgtt | tggagcacct | taacatggaa | gataatgata | 1200 |
| ttccaggcat | aaaagcaat | atgttcacag | gattgataaa | cctgaaatac | ttaagtctat | 1260 |
| ccaactcctt | tacaagtttg | cgaactttga | caaatgaaac | atttgtatca | cttgctcatt | 1320 |
| ctcccttaca | catactcaac | ctaaccaaga | ataaaatctc | aaaaatagag | agtgatgctt | 1380 |
| tctcttggtt | gggccaccta | gaagtacttg | acctgggcct | taatgaaatt | gggcaagaac | 1440 |
| tcacaggcca | ggaatggaga | ggtctagaaa | atattttcga | aatctatctt | tcctacaaca | 1500 |
| agtacctgca | gctgactagg | aactcctttg | ccttggtccc | aagccttcaa | cgactgatgc | 1560 |
| tccgaagggt | ggcccttaaa | aatgtggata | gctctccttc | accattccag | cctcttcgta | 1620 |
| acttgaccat | tctggatcta | agcaacaaca | acatagccaa | cataaatgat | gacatgttgg | 1680 |
| agggtcttga | gaaactagaa | attctcgatt | tgcagcataa | caacttagca | cggctctgga | 1740 |
| aacacgcaaa | ccctggtggt | cccatttatt | tcctaaaggg | tctgtctcac | ctccacatcc | 1800 |
| ttaacttgga | gtccaacggc | tttgacgaga | tcccagttga | ggtcttcaag | gatttatttg | 1860 |
| aactaaagat | catcgattta | ggattgaata | atttaaacac | acttccagca | tctgtcttta | 1920 |
| ataatcaggt | gtctctaaag | tcattgaacc | ttcagaagaa | tctcataaca | tccgttgaga | 1980 |
| agaaggtttt | cgggccagct | ttcaggaacc | tgactgagtt | agatatgcgc | tttaatccct | 2040 |
| ttgattgcac | gtgtgaaagt | attgcctggt | ttgttaattg | gattaacgag | acccatacca | 2100 |
| acatccctga | gctgtcaagc | cactaccttt | gcaacactcc | acctcactat | catgggttcc | 2160 |
| cagtgagact | ttttgataca | tcatcttgca | aagacagtgc | cccctttgaa | ctcttttca | 2220 |

-continued

```
tgatcaatac cagtatcctg ttgattttta tctttattgt acttctcatc cactttgagg   2280
gctggaggat atctttttat tggaatgttt cagtacatcg agttcttggt ttcaaagaaa   2340
tagacagaca gacagaacag tttgaatatg cagcatatat aattcatgcc tataaagata   2400
aggattgggt ctgggaacat ttctcttcaa tggaaaagga agaccaatct ctcaaatttt   2460
gtctggaaga aagggacttt gaggcgggtg ttttttgaact agaagcaatt gttaacagca   2520
tcaaaagaag cagaaaaatt attttttgtta taacacacca tctattaaaa gacccattat   2580
gcaaaagatt caaggtacat catgcagttc aacaagctat tgaacaaaat ctggattcca   2640
ttatattggt tttccttgag gagattccag attataaact gaaccatgca ctctgtttgc   2700
gaagaggaat gtttaaatct cactgcatct tgaactggcc agttcagaaa gaacggatag   2760
gtgcctttcg tcataaattg caagtagcac ttggatccaa aaactctgta cattaaattt   2820
atttaaatat tcaattagca aaggagaaac tttctcaatt taaaaagttc tatggcaaat   2880
ttaagttttc cataaaggtg ttataatttg tttattcata tttgtaaatg attatattct   2940
atcacaatta catctcttct aggaaaatgt gtctccttat ttcaggccta ttttgacaa   3000 ttgacttaat tttacccaaa ataaaacata taagcacgta aaaaaaaaa aaaaaaa     3057
```

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 163
gcagttcttg gaggttctcc                                                20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 164
cagacctctc cattcctggc                                                20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe

```
<220> FEATURE:
<221> NAME/KEY: modified_base
<222> LOCATION: (17)..(20)
<223> OTHER INFORMATION: 2'-OMe

<400> SEQUENCE: 165
tgaggttctt ctggaggttc                                               20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: modified_base
<222> LOCATION: (1)..(4)
<223> OTHER INFORMATION: 2'-OMe
<220> FEATURE:
<221> NAME/KEY: modified_base
<222> LOCATION: (17)..(20)
<223> OTHER INFORMATION: 2'-OMe

<400> SEQUENCE: 166
gctcaatagc ttgctgaact                                               20
```